(12) United States Patent
Ozdemir et al.

(10) Patent No.: US 12,343,419 B2
(45) Date of Patent: Jul. 1, 2025

(54) TOPICAL COMPOSITION

(71) Applicant: Framergy Inc., College Station, TX (US)

(72) Inventors: Osman Koray Ozdemir, Tomball, TX (US); Jason Ornstein, London (GB); Anne Boehme, Tomball, TX (US)

(73) Assignee: Framergy Inc., College Station, TX (US)

( * ) Notice: Subject to any disclaimer, the term of this patent is extended or adjusted under 35 U.S.C. 154(b) by 770 days.

(21) Appl. No.: 17/599,761

(22) PCT Filed: Mar. 29, 2019

(86) PCT No.: PCT/US2019/024833
§ 371 (c)(1),
(2) Date: Sep. 29, 2021

(87) PCT Pub. No.: WO2020/204876
PCT Pub. Date: Oct. 8, 2020

(65) Prior Publication Data
US 2022/0142889 A1    May 12, 2022

(51) Int. Cl.
*A61K 8/58* (2006.01)
*A61K 8/02* (2006.01)
*A61K 8/31* (2006.01)
*A61Q 17/04* (2006.01)

(52) U.S. Cl.
CPC .............. *A61K 8/58* (2013.01); *A61K 8/0279* (2013.01); *A61K 8/31* (2013.01); *A61Q 17/04* (2013.01); *A61K 2800/652* (2013.01)

(58) Field of Classification Search
CPC ........ A61Q 17/04; A61K 8/58; A61K 8/0279; A61K 8/31; A61K 2800/652
See application file for complete search history.

(56) References Cited

U.S. PATENT DOCUMENTS

| 8,940,392 B2 | 1/2015 | Serre et al. | |
| 2009/0149419 A1* | 6/2009 | Amit | A61K 31/726 514/54 |
| 2011/0052650 A1* | 3/2011 | Morris | A61K 8/494 424/409 |
| 2016/0346759 A1* | 12/2016 | Zhou | C01B 3/508 |

FOREIGN PATENT DOCUMENTS

| DE | 102016220085 A1 | 4/2018 |
| FR | 2942229 A1 | 8/2010 |

OTHER PUBLICATIONS

Zhu et al., "Titanium-based metal-organic frameworks for photocatalytic applications," in Coordination Chemistry Reviews 359 (2018) 80-101. (Year: 2018).*

(Continued)

*Primary Examiner* — Blessing M Fubara
(74) *Attorney, Agent, or Firm* — REISING ETHINGTON, P.C.

(57) ABSTRACT

A composition comprising a titanium metal organic framework and a dermatologically acceptable carrier is presented, the use of the same as a sunscreen or cosmetic. A method of protecting skin from the effect of UV radiation comprising administering the same to skin.

19 Claims, 6 Drawing Sheets

(56) References Cited

OTHER PUBLICATIONS

International Search Report for International Application No. PCT/US2019/024833 dated Nov. 20, 2019 (4 pages).
Meenakshi Dan-Hardi et al: "A New Photoactive Crystalline Highly Porous Titanium(IV) Dicarboxylate", Journal of the American Chemical Society, vol. 131, No. 31, Aug. 12, 2009 (Aug. 12, 2009), pp. 10857-10859, XP055326137, US.
Christopher H. Hendon et al: "Engineering the Optical Response of the Titanium-MIL-125 Metal-Organic Framework through Ligand Functionalization", Journal of the American Chemical Socitey, vol. 135, No. 30, Jul. 10, 2013, pp. 10942-10945, XP055544522, US.
International Preliminary Report on Patentability for International Application No. PCT/US2019/024833 dated Sep. 28, 2021 (6 pages).

* cited by examiner

TOPICAL COMPOSITION

TECHNICAL FIELD

The present disclosure relates to compositions comprising a metal organic framework (MOF) which absorb ultra violet (UV) light, the use thereof as well as the absorption of harmful byproducts of radical oxygen species.

BACKGROUND

Ultra Violet (UV) light from the sun is well known as an initiator of sun burn, and promoter of cancer, which has led to the development of sunscreens and cosmetics containing sunscreens which inhibit the effects of UV light. Solar ultra violet radiations (UVR) is divided into three categories: UV-C (200-280 nm), UV-B (280-320 nm) and UV-A (320-400 nm). UV-C is the most biologically damaging radiation, but it is filtered out by ozone layer. Sunscreens are chemical compositions that absorb or block UV rays and show a variety of immunosuppressive effects of sunlight. For this reason, sales of sunscreen in the US are growing. Cosmetic products containing ultraviolet light filtering agents are rapidly being developed and entering the marketplace. These advanced multifunctional formulations are intended to deliver both cosmetic and protective benefits.

Active UV filters used in sunscreens can be chemically classified into two groups, organic and inorganic. The former are aromatic compounds with a carbonyl group, which react with UV photons. The latter include several materials, but the only ones approved by the United States (US) Food and Drug Administration (FDA) are titanium dioxide and zinc oxide. These two inorganic materials can reflect, scatter and/or absorb UV light. One advantage over organic actives are their general improvement in the UV-B range, and the fact that organic actives are known to break down under UV radiation more readily.

Titanium dioxide was first established as a sunscreen in 1952, and since hundreds of patents have suggested compositions from this material for sunblock. The titanium node is known to block UVA and UVB light through scattering. This effect can protect the human skin from cell DNA damage by UV radiation. Due to this effect, Titanium dioxide is a sought-after ingredient in foundation and other cosmetics because of light scattering capability and color additive properties.

Unfortunately, commercial sunscreens which use titanium dioxide can generate free radical reactive oxygen species (ROS) that damage the skin and may cause DNA damage. Free radicals can be defined as a reactive chemical species having a single unpaired electron outer orbit. Additives in sunscreens can react with ROS to form less harmful products, but these byproducts are still are potentially dangerous for the skin as they induce sensitization and skin irritation. Based on the current evidence, the risk of titanium dioxide in sunscreen is considered negligible to humans and it is recommended up to 25 percent of the formulation by weight in the United States Pharmacopia. Nevertheless, an increase in cases of melanoma are thought to be the result of increased use of sunscreens.

SUMMARY

In an embodiment, a composition may include a titanium metal organic framework and a dermatologically acceptable carrier.

In another embodiment, a method of protecting skin from the effect of ultra-violet (UV) radiation may include administering an effective amount of a composition comprising a titanium metal organic framework (MOF) and a dermatologically acceptable carrier.

DETAILED DESCRIPTION

Figure 1:
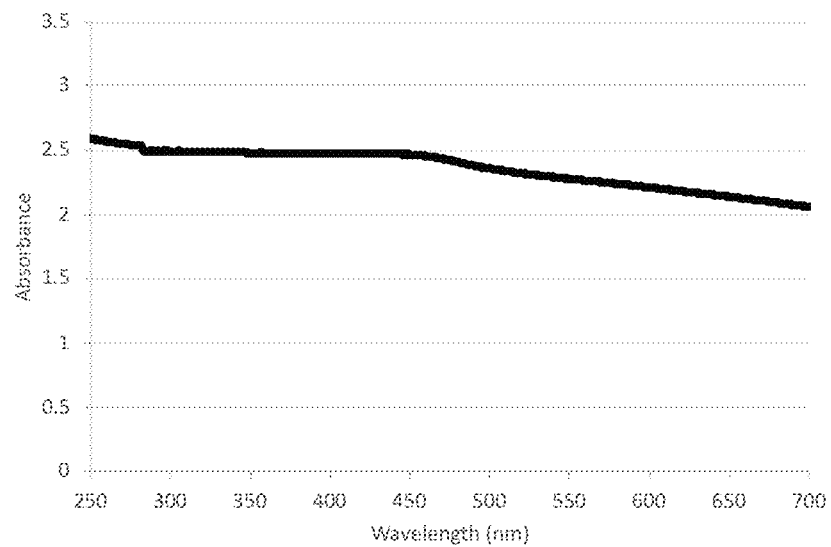
FIG. 1 is a graph showing ultraviolet ray absorption by MIL-125$NH_2$ dissolved in Squalene in an expected saturation (Composition 2).
Figure 2:
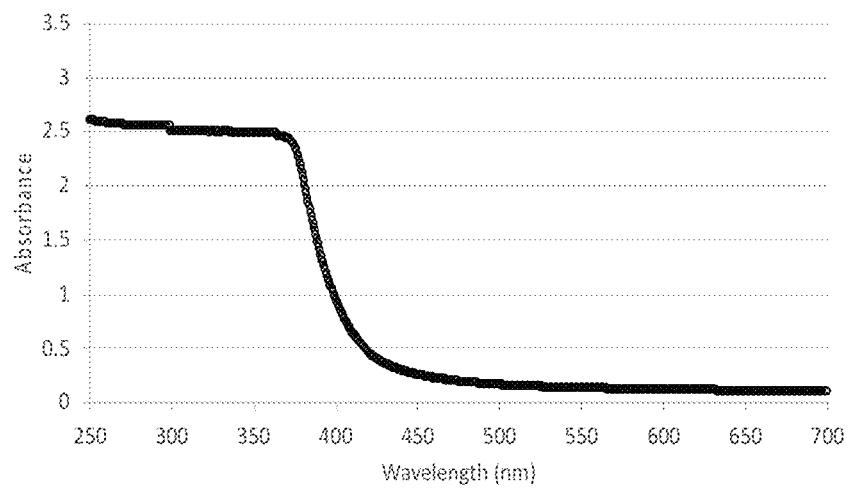
FIG. 2. is a graph showing ultraviolet ray absorption by MIL-125$NH_2$ dissolved in
Squalene in a low saturation (Composition 1).
Figure 3:
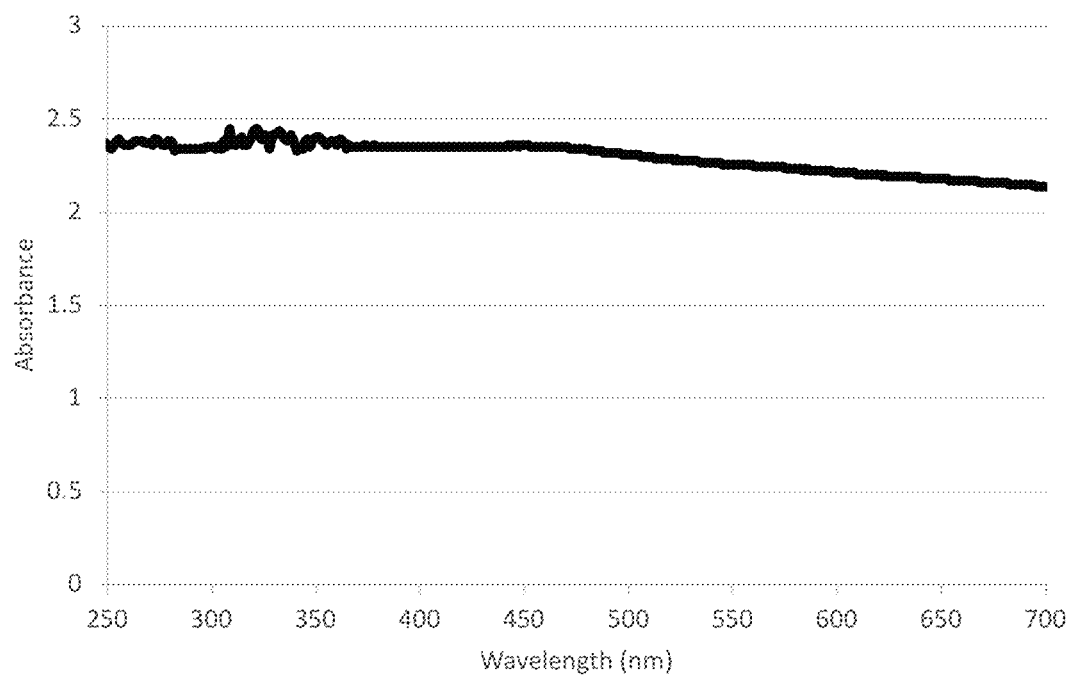
FIG. 3. is a graph showing ultraviolet ray absorption by MIL-125$NH_2$ dissolved in Squalene in a high saturation (Composition 3).
Figure 4:
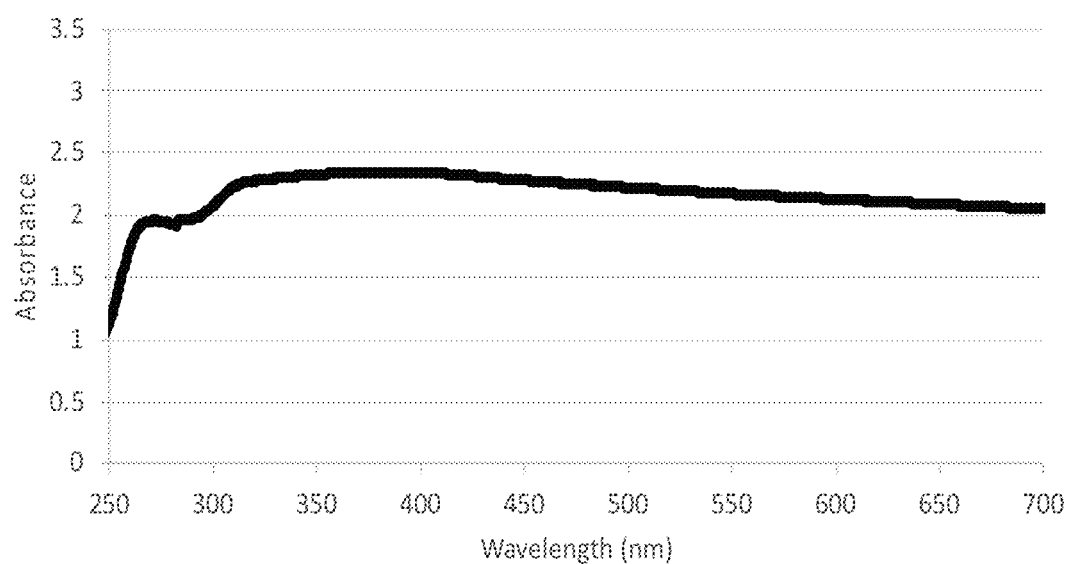
FIG. 4. is a graph showing ultraviolet ray absorption by MIL-177HT dissolved in Squalene in an expected saturation (Composition 4).
Figure 5:
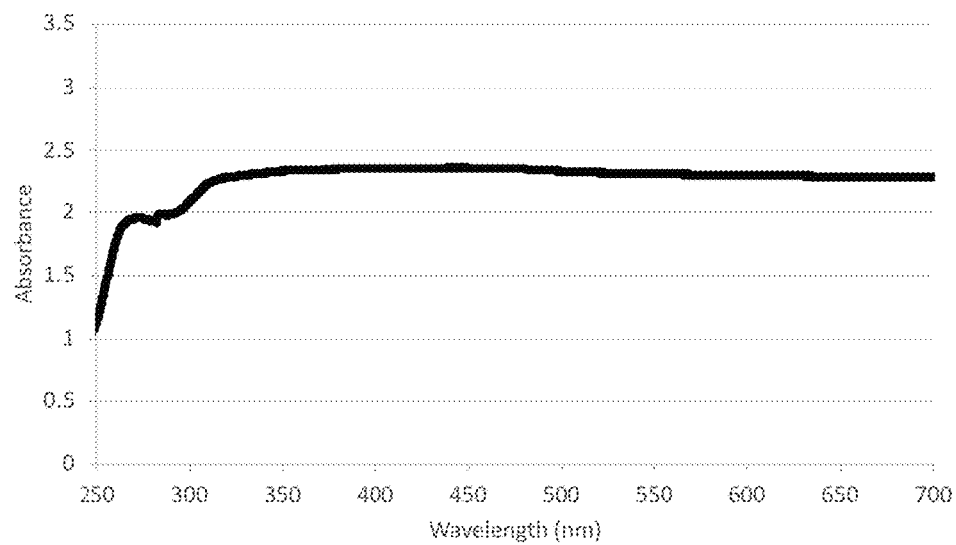
FIG. 5. is a is a graph showing ultraviolet ray absorption by MIL-125$NH_2$ dissolved in Oxybenzone in an expected saturation (Composition 5).
Figure 6:
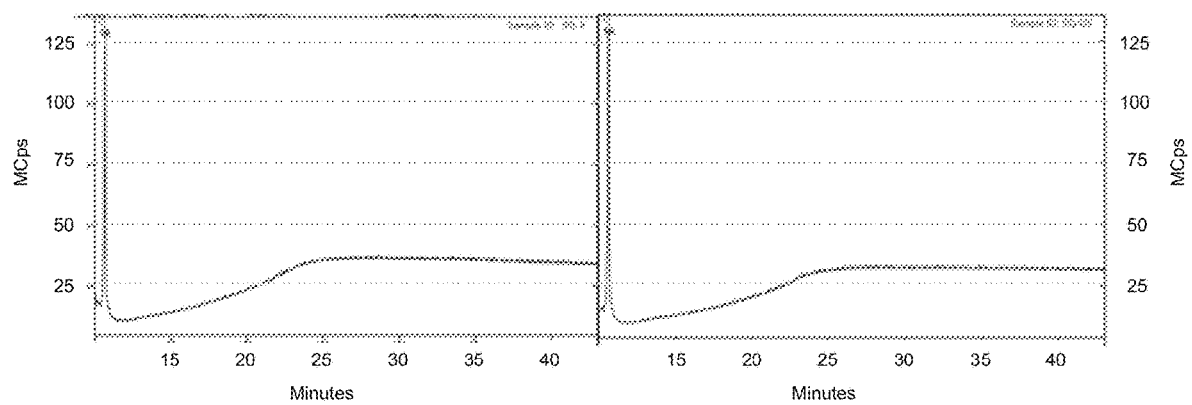
FIG. 6 is a GC chromatogram analysis of squalene levels for a composition of Squalene oil before and after UV Exposure, showing no change in squalene as a percent of the solution.
Figure 7:
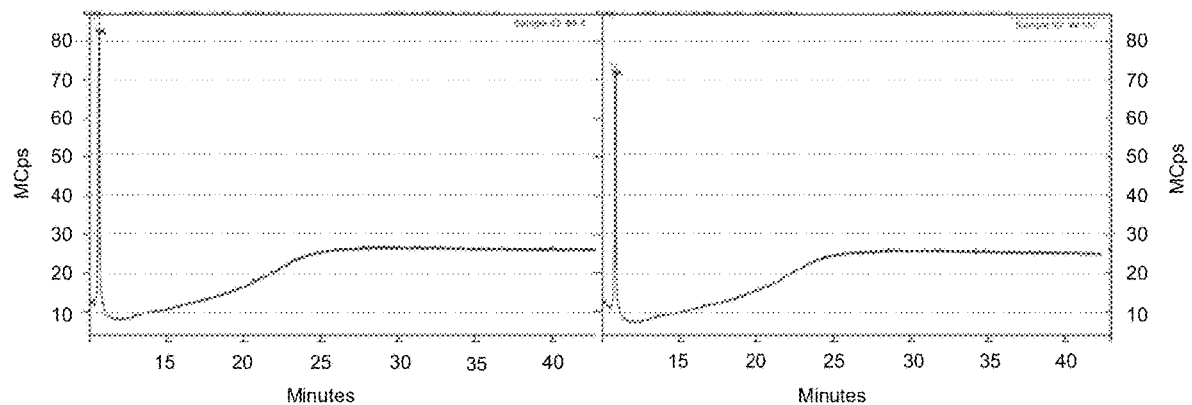
FIG. 7. is a GC chromatogram analysis of squalene levels for a composition of MIL-125$NH_2$ dissolved in Squalene in a high saturation (Composition 3) before and after UV Exposure, showing a decrease in squalene through oxidation by ROS, and no evidence of monohydroperoxide isomers.
Figure 8:
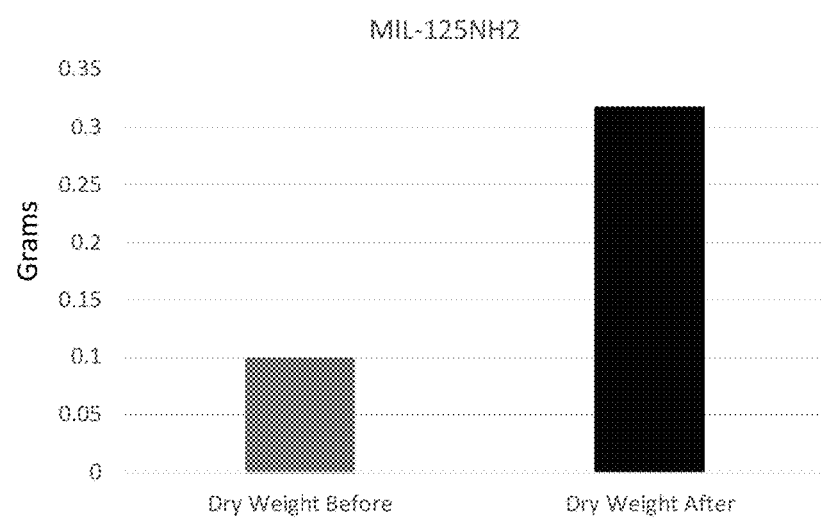
FIG. 8. is a graph of the weight increase of MIL-125$NH_2$ to determine the weight percent uptake of hydrogen peroxides by MIL-125$NH_2$.
Figure 9:
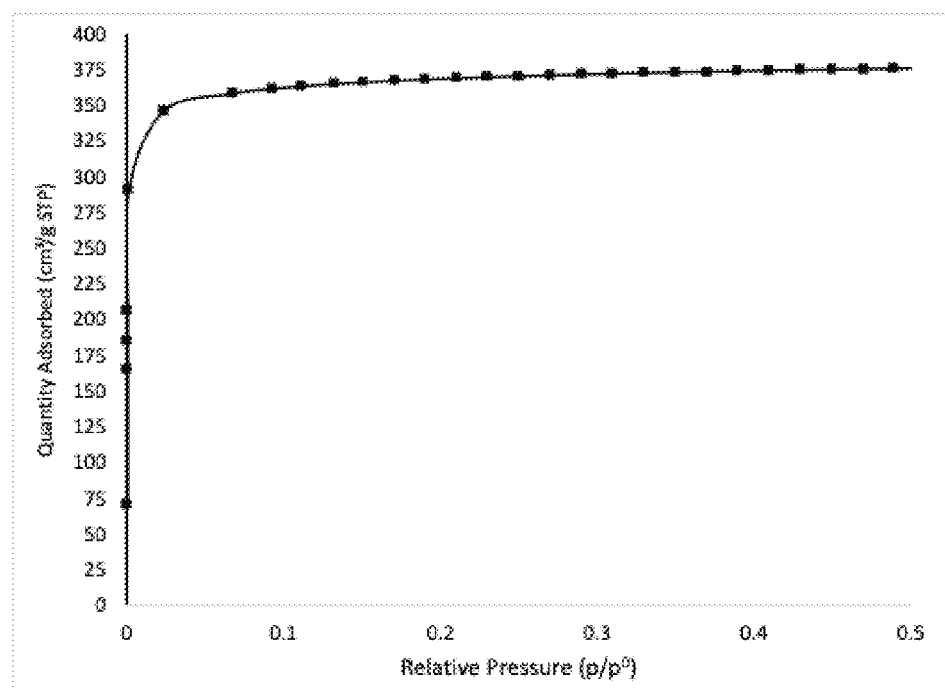
FIG. 9. is a graph of $N_2$ adsorption over MIL-125$NH_2$ to determine surface area.
Figure 10:
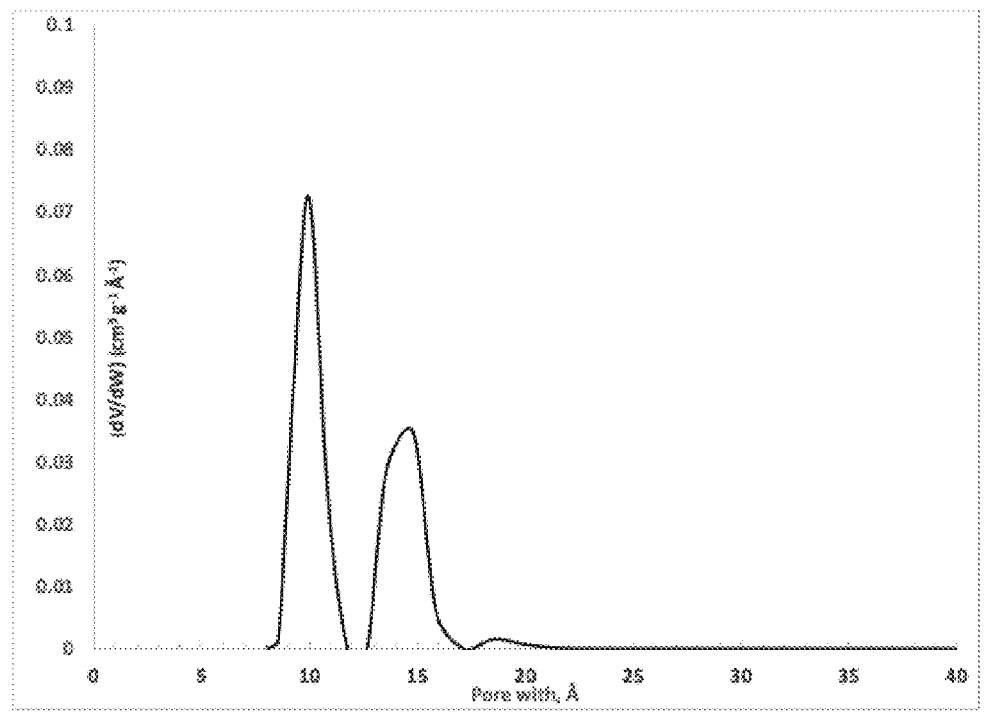
FIG. 10. is a an analysis of pore size distribution of MIL-125$NH_2$ to determine average pore size(s).
Figure 11:
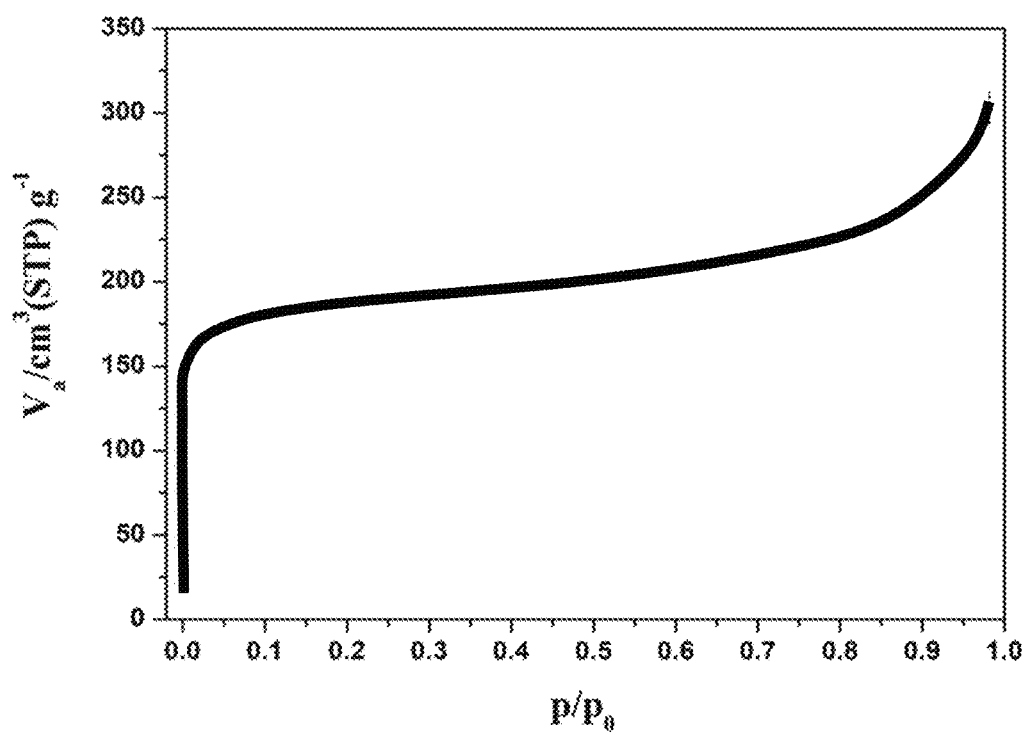
FIG. 11. is a graph of $N_2$ adsorption over MIL-177 to determine surface area.

The present disclosure, per an embodiment, relates to a composition comprising a titanium metal organic framework and a dermatologically acceptable carrier, the use of the same for protecting skin from the effect of UV radiation, for example as a sunscreen or cosmetic, and a method of protecting skin from the effect of UV radiation comprising administering the same to skin.

Metal-Organic Frameworks (MOFs) have garnered significant interests in the last two decades due to their promising potential in many applications such as gas adsorption, separation, catalysis and sensing. Compared with other porous materials such as zeolite and mesoporous silica, MOFs are based on crystalline porous structures tunable on the atomic scale, which can be designed and functionalized by judicious choice of metal nodes and modification of the organic linkers. However, little research has been done in the application of MOFs for cosmetic purposes.

As an extensively used photocatalyst, $TiO_2$ has several drawbacks such as low surface area. However, when acting as nodes in a MOF, titanium oxo clusters are periodically arranged and separated by organic linkers, which leads to a highly accessible and large surface area.

Unfortunately, the high reactivity of the titanium cation has made the discovery of titanium MOFs challenging.

In 2009 and 2010, the first stable titanium MOFs, MIL-125 and MIL-125NH$_2$, were reported and showed photocatalytic activity. Though highly sought after as a photocatalyst, only a handful of structures have been proven. Of these known structures, several have been tested for UV absorption with the goal of understanding their use as a photocatalyst.

MIL-125NH$_2$ is made from the monoanmimated bdc-NH$_2$ linker and is a well-known photocatalyst. The bdc-NH$_2$ linker enhances UV adsorption over 350 nm. The addition of further amine functionality in the linker can add marginal increases in UVA adsorption. Along with its metal node, MIL-125NH$_2$ undergoes photo induced charge separation. MIL-177HT is another titanium MOF with photocatalytic capacity, but where the linker does not enhances UV adsorption.

Testing was done to define Ti MOFs for applications in photocatalytic oxidation, CO$_2$ reduction, hydrogen evolution, organic pollutant degradation, polymerization, deoximation and photocatalytic sensors. And while a great deal of effort has been put into studying Ti MOFs as photocatalyst, the inventors are not aware of any one preparing a composition comprising of limited amounts of Ti metal organic frameworks and containing a dermatologically acceptable carrier for use as a sunscreen.

An object of the disclosure, per an embodiment, therefore, is to provide a sunscreen composition comprising metal organic frameworks (MOF) which absorbs ultra violet (UV) light. This is especially useful when considering that Ti MOFs are known to have low toxicity. But, in consideration of market regulation, the inorganic comprising MOF cannot be the majority of the composition, and should be far lower if a weight percent to the composition. In one embodiment, the MOF weight percent of the composition was 0.0058%, and showed UV absorption. In one embodiment, the MOF weight percent of the composition was 0.293%, and showed UV absorption. In one embodiment, the MOF weight percent of the of the composition was 0.579%, and showed UV absorption. In light of both regulation and commercial acceptability of color, extremely small amounts of Ti MOF were found to be dilutable in organic carriers resulting in no or limited color change and extreme levels of UV absorption.

According to an embodiment, there is provided a composition comprising a titanium metal organic framework and a dermatologically acceptable carrier. In one embodiment, the titanium metal organic framework is dispersed in the dermatologically acceptable carrier. In one embodiment, the composition is for topical administration, for example to human skin. In one embodiment, the composition is a sunscreen composition. In one embodiment, the metal organic framework is made up of titanium metal clusters and carboxyolate ligands. For example, the titanium metal ion is coordinated to at least one aromatic di-, tri-, or tetracarboxylic acid. An embodiment therefore provides that all known titanium metal organic frameworks can be used in the composition, e.g. sunscreen composition.

In one embodiment, the composition comprising a metal organic framework absorbs ultra violet light. For example, the composition comprising metal organic frameworks absorbs ultra violet light in the UV-C (200-280 nm), UV-B (280-320 nm) and UV-A (320-400 nm) spectrums, where absorbence (A.=log I$_0$/I) is greater than one, greater than two, greater than two and a half, and greater than three. An embodiment therefore provides UV absorption through an inorganic containing composition, e.g. sunscreen composition, that far exceeds anything that has been achieved before.

In one embodiment, the titanium metal organic framework comprises a metal cluster selected from Ti$_8$O$_8$(OH)$_4$ or Ti$_{12}$O$_{15}$.

In one embodiment, the titanium metal organic framework comprises a ligand represented by the formula:

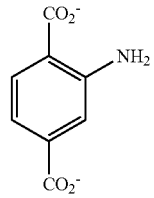

In one embodiment, the titanium metal organic framework comprises a ligand represented by the formula:

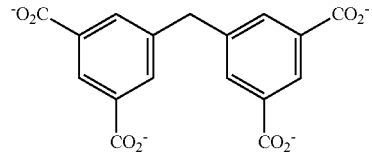

In one embodiment, the titanium metal organic framework comprises Ti$_8$O$_8$(OH)$_4$ and ligands represented by the formula:

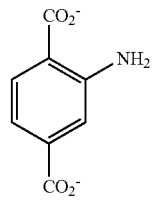

In one embodiment, the titanium metal organic framework comprises Ti$_{12}$O$_{15}$ and ligands represented by the formula:

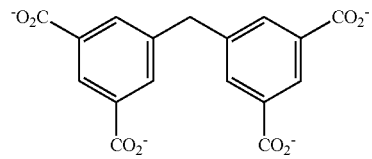

In one embodiment, the metal organic framework comprises (i) a metal cluster; and (ii) one or more ligands; wherein the metal cluster comprises titanium.

In one embodiment, the metal cluster comprises the formula Ti$_a$X$_b$O$_c$, wherein X is a metal selected from Group 2 through Group 16, for example a transition metal, and wherein a+b=c. For example, X is selected from Al, Fe, Ti, Co, Mn, Zn, Ni, Mg, Cu, and Ca. For example, the metal cluster has the formula TiO, Ti$_8$O$_8$ or Ti$_{16}$O$_{16}$.

Specifically, the metal organic framework comprises a metal cluster comprising the formula TiO, Ti$_8$O$_8$ or Ti$_{16}$O$_{16}$ and one or more ligands derived from 1,4-benzene-dicarboxylic acid.

In one embodiment, the metal organic framework comprises a metal cluster comprising the formula Ti, $Ti_2$, TiO, $TiO_{0.5}$, $Ti_3O_2$, $Ti_3O_3$, $Ti_3O$, $Ti_7O_6$, $Ti_6O_6$, $Ti_8O_8$, or $Ti_{16}O_{16}$ and one or more ligands derived from methylenediphosphonate, elthlyenediphosphonate, propylenediphosphonate, N,N'-piperazinebismehtylenephosphonate, terephthalate, 1,4-cyclohexanedicarboxylate, 1,4-benzenedicarboxylate, tetrakis(4-carboxyphenyl)porphyrin, 1,4-phenylenebis(methanylylidene)bis(azanylylidene)dibenzoate, bisphenyl-4,4' diylbis-(methanylylidene)bis(azanylylidene)dibenzoate, 2,5-dihydroxyterephthalate, hydroquinone, 2,7-dihydroxynaphthalene, resourcinol, 4,4' dihydroxy-biphenyl, 2,3,6,7,9,11-hexahydroxytriphenylene, and 4-picoline.

In one embodiment the titanium metal organic framework comprises formula (I).

$$Ti_aO_b(OH)_c[(^-OOC)—X\text{-}\#]_d \qquad (I)$$

In formula (I):

X is an organic spacer and represents a saturated or unsaturated, linear or branched, aliphatic chain having 2 to 12 carbon atoms; a monocyclic, bicyclic or tricyclic hydrocarbon-based aromatic group that is unsubstituted or that is substituted by one or more substituents R independently chosen from a halogen atom and amino, nitro, hydroxyl, C1-C4 trifluoroalkyl and C1-C4 alkyl groups: a benzophenone group; a monocyclic or bicyclic heteroaromatic group in which the ring(s) is(are) 5- or 6-membered ring(s), said group containing at least one heteroatom chosen from nitrogen and sulfur and being unsubstituted or substituted by one or more substituents R independently chosen from a halogen atom and amino, nitro, hydroxyl, C1-C4 trifluoroalkyl and C1-C4 alkyl groups;

a and b, which are identical or different, are integers varying from 1 to 16 inclusively; c and d, which are identical or different, are integers varying from 1 to 32 inclusively; the indices a, b, c and d adhere to the relation $4a=2b+c+d$;

the titanium atoms form a purely inorganic elementary building block constituted of titanium oxo complexes;

\# is the point through which two units of formula (I) are joined together; \# represents a covalent bond between a carbon atom belonging to the spacer X and the carbon atom of a carboxylate group $COO^-$ of another unit of formula (I) and in which the two oxygen atoms of the carboxylate group belong respectively to two adjacent octahedral titanium oxo complexes of an elementary building block of said other unit of formula (I);

In some embodiments, a single X may be shared between two or more units of formula (I).

In one embodiment, X may be made of linear alkyl chains such as ethyl, propyl, butyl, pentyl, hexyl, heptyl, octyl, nonyl, decyl, undecyl and dodecyl chains; linear alkene chains such as ethylene, propylene, butylene, pentylene, hexylene, heptylene, octylene, nonylene, decylene, undecylene and dodecylene; alkyne chains such as ethyne, propyne, butyne, pentyne, hexyne, heptyne, octyne, nonyne, decyne, undecyne and dodecyne. Among such chains, C1-C4 alkyl chains and C2-C4 alkene or alkyne chains are preferred, per certain embodiments.

In one embodiment, X may be made of phenylene; chlorophenylene; bromophenylene; aminophenylene; nitrophenylene; mono-, di- or tetramethylphenylene; mono- or diethenylphenylene; mono- or dihydroxyphenylene; biphenylene; diphenyldiazene; naphthalene and anthracene groups.

In one embodiment, X may be made of thiophene, bithiophene, pyridine, bipyridine and pyrazine rings.

In one embodiment, the subunit $[^-OOC—X\text{-}\#]$ is chosen from the groups of formulae (II-1) to (II-13) below:

(II-1)

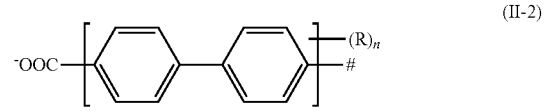

(II-2)

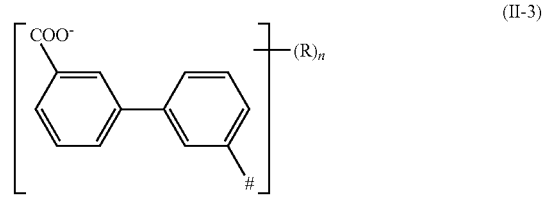

(II-3)

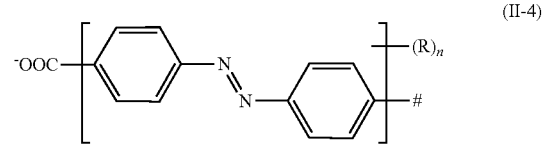

(II-4)

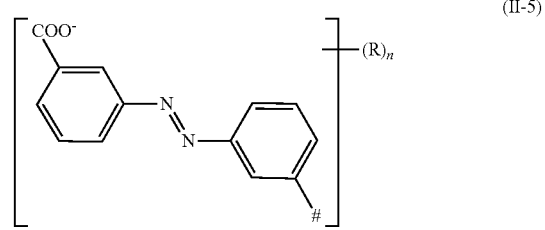

(II-5)

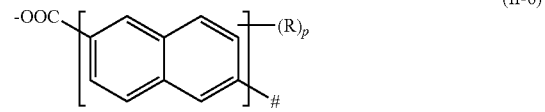

(II-6)

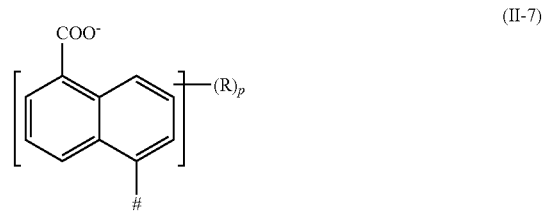

(II-7)

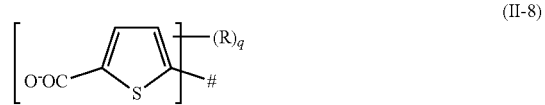

(II-8)

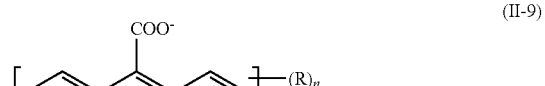

(II-9)

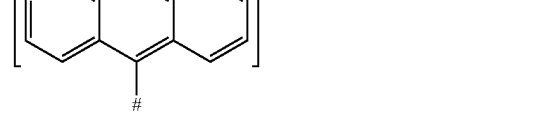

(II-10)

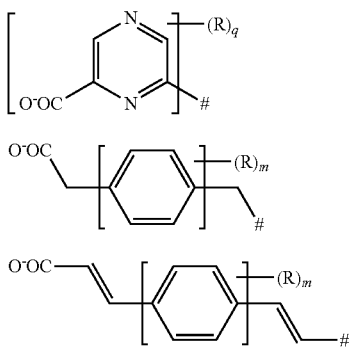

(II-11)

(II-12)

(II-13)

in which:
R is a halogen atom, an amino, nitro, hydroxyl, C1-C4 trifluoroalkyl or C1-C4 alkyl group;
m is an integer ranging from 0 to 4;
n is an integer ranging from 0 to 8;
p is an integer ranging from 0 to 6;
q is an integer ranging from 0 to 2; and
r is an integer ranging from 0 to 3.

In one embodiment, formula (II-1) is selected from, phenyl-1-carboxylate, phenyl-2-amino-1-carboxylate, phenyl-2,5-dihydroxy-1-carboxylate and phenyl-2-chloro-1-carboxylate.

In one embodiment, formula (II-4) is selected from azobenzene-4-carboxylate, azobenzene-3,3'-dichloro-4-carboxylate and azobenzene-3,3'-dihydroxy-4-carboxylate.

In one embodiment, formula (II-8) is selected from thiophene-2-carboxylate and 3,4-dihydroxythiophene-2-carboxylate.

In one embodiment, the subunit [⁻OOC—X-#] is selected from phenyl-1-carboxylate, phenyl-2-amino-1-carboxylate, and thiophene-2-carboxylate.

In one embodiment, the subunits of formula (I) as defined previously, is selected from the subunits of formula (I-1) below:

In formula (I-1):
X and # are as defined previously;
the titanium atoms form a purely inorganic elementary building block constituted of 8 octahedral titanium oxo complexes each comprising a central titanium atom surrounded by 6 oxygen atoms, said octahedral titanium oxo complexes being joined together either by a common edge, or by a common apex, in both cases by means of oxo-O— or hydroxo-OH— bridges; said building blocks being connected together in the three dimensions of space by organic spacers X; it being understood that each of the building blocks is connected to 12 organic spacers by means of carboxylate groups COO⁻ in which each of the two oxygen atoms is an integral part of two adjacent titanium oxo complexes.

In the subunits of formula (I-1), an elementary building block (or wheel of octahedral titanium oxo complexes) therefore contains 36 oxygen atoms connected to eight titanium atoms alternately either via a common edge involving two oxo or hydroxo bridges or by a common apex involving a single oxo or hydroxo bridge, or by means of carboxylate groups.

In one embodiment, the metal cluster comprises the formula $Ti_{12}O_{15}$ or $Ti_{12}O_{18}$ and the ligand is derived from the following groups:

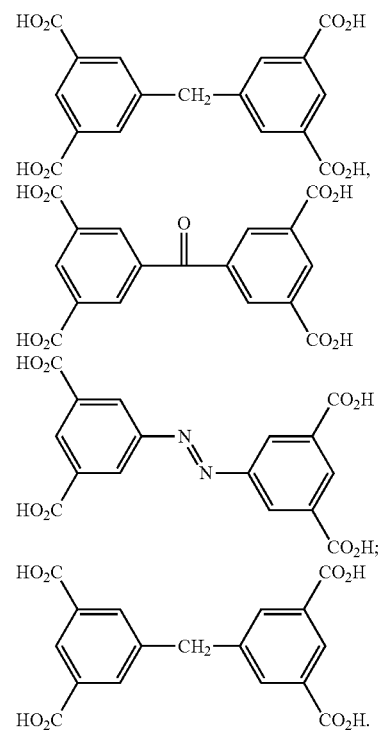

In one embodiment, the metal organic framework comprises a metal cluster of formula $Ti_{12}O_{15}$, a ligand derived from the above group, and formate (as an additional ligand).

In one embodiment, the titanium metal organic framework is selected from the following:

| Name | Molecular formula | Ligand (L) |
| --- | --- | --- |
| MIL-22 | $Ti^{IV}{}_3O_2(H_2O)_2(L)_2 \cdot 2H_2O$ | Methylenediphosphonate |
| MIL-25$_2$ | $Ti^{IV}(L)$ | Ethylenediphosphonate |
| MIL-25$_3$ | $Ti^{IV}(L)$ | Propylenediphosphonate |
| MIL-91 | $Ti^{IV}O(H_2\text{-}L) \cdot nH_2O$ (n ~4.5) | N,N'-piperazinebismethylenephosphonate |
| MIL-125 | $Ti^{IV}{}_8O_8(OH)_4(L)_6$ | Terephthalate |
| COK-69$_{op\&c}$ | $Ti^{IV}{}_3O_3(L)_3 \cdot DMF$ | 1,4-Cyclohexanedicarboxylate |
| MIL-101 (Ti) | $Ti^{III}{}_3O(OCH_2CH_3)$ $(L)_3 \cdot 2DMF$ | 1,4-Benzenedicarboxylate |
| PCN-22 | $Ti^{IV}{}_7O_6(L)_{12} \cdot 2DEF$ | Tetrakis(4-carboxyphenyl)porphyrin |
| MOF-901 | $Ti^{IV}{}_6O_6(OCH_3)_6(L)_3$ | 1,4-Phenylenebis(methanylylidene) bis(azanylylidene)dibenzoate |

-continued

| Name | Molecular formula | Ligand (L) |
|---|---|---|
| MOF-902 | $Ti^{IV}_6O_6(OCH_3)_6(L)_3$ | Biphenyl-4,4-diylbis-(methanylylidene)bis(azanylylidene)dibenzoate |
| NTU-9 | $Ti^{IV}_2(H\text{-}L)_2(H_2\text{-}L)_n$ | 2,5-Dihydroxyterephthalate |
| MIL-167 | $Ti^{IV}(L)_{1.5}(Et_2MeNH)_2 \cdot nH_2O$ | 2,5-Dihydroxyterephthalate |
| MIL-168 | $Ti^{IV}(L)(cat) \cdot 2DEAH$ | 2,5-Dihydroxyterephthalate |
| MIL-169 | $Ti^{IV}O_{0.5}(L)(H_2O)(H_2\text{-}pip)_{0.5} \cdot nH_2O$ | 2,5-Dihydroxyterephthalate |
| Ti-phenol | $[Ti^{IV}(L)(H\text{-}L)]_2(\mu\text{-}H\text{-}L)_2$ | Hydroquinone |
| Ti-phenol | $Ti^{IV}(L)_2 \cdot py_2$ | Hydroquinone |
| Ti-phenol | $Ti^{IV}_2(\mu_{1,4}\text{-}L)_2(\mu_{1,4}\text{-}H\text{-}L)_2(\mu\text{-}H\text{-}L)_2$ | Hydroquinone |
| Ti-phenol | $Ti^{IV}_2(\mu_{1,4}\text{-}L)_2(\mu_{1,4}\text{:}\eta^2,\eta^1\text{-}L)_2(OH_2)_2(H_2O)_2(H_2\text{-}L) \cdot x(CH_3CN)$ (x = 1 or 2) | Hydroquinone |
| Ti-phenol | $Ti^{IV}_2(\mu_{1,7}\text{-}L)_2(\mu_{1,7}\text{:}\eta^2,\eta^1\text{-}H\text{-}L)_2(O^iPr)_2$ | 2,7-Dihydroxy-naphthalene |
| Ti-phenol | $Ti^{IV}(\mu_{1,4}\text{-}L)_2py_2$ | Hydroquinone |
| Ti-phenol | $Ti^{IV}(\mu_{1,4}\text{-}L)_2 \cdot py_2 \cdot py$ | Hydroquinone |
| Ti-phenol | $Ti^{IV}(\mu_{1,4}\text{-}L)_2 \cdot (4\text{-}Ph\text{-}py)_2$ | Hydroquinone |
| Ti-phenol | $Ti^{IV}(\mu_{1,3}\text{-}L)_2 \cdot py_2$ | Resorcinol |
| Ti-phenol | $Ti^{IV}(\mu_{1,3}\text{-}L)_2 \cdot (4\text{-}Ph\text{-}py)_2$ | Resorcinol |
| Ti-phenol | $Ti^{IV}(\mu_{1,6}\text{:}\eta^2\eta^1\text{-}4,4'\text{-}L)_{0.5}(\mu_{1,6}\text{:}\eta^2,\eta^1\text{-}4,4'\text{-}L)(O^iPr)(HO^iPr)_2 \cdot THF$ | 4,4'-Dihydroxy-biphenyl |
| Ti-phenol | $Ti^{IV}(\mu_{1,3}\text{-}1,4\text{-}L)(\mu_{1,3}\text{-}1,3\text{-}L)(1,3\text{-}H\text{-}L)(HO^iPr)_2$ | Resorcinol |
| Ti-phenol | $Ti^{IV}(\mu_{2,7}\text{-}L)_2 \cdot py_2$ | 2,7-Dihydroxy-naphthalene |
| Ti-phenol | $Ti^{IV}(\mu_{2,7}\text{-}L)_2(4\text{-picoline})_{2.5}$ | 2,7-Dihydroxy-naphthalene |
| Ti-CAT-5 | $Ti^{IV}(L) \cdot 2DMA$ | 2,3,6,7,9,11-Hexahydroxytriphenylene |

In one embodiment, the composition comprises a titanium metal organic framework having a BET surface area greater than 200 m$^2$/g, greater than 300 m$^2$/g, greater than 400 m$^2$/g, or greater than 500 m$^2$/g.

In one embodiment, the composition comprises a titanium metal organic framework having an average pore size between 5 Å and 50Å.

In one embodiment, the composition comprises a titanium metal organic framework in an amount greater than 0.001 wt % of the composition. For example, the composition may comprise up to 50 wt % of the composition. For example, the composition may comprise between 0.001 wt % and 50 wt % titanium metal organic framework, between 0.002 wt % and 40 wt %, between 0.003 wt % and 30 wt %, or between 0.005 wt % and 25 wt % titanium metal organic framework of the composition. In particular, the amount of titanium metal organic framework does not exceed regulatory standards.

The composition comprises a dermatologically acceptable carrier which may also be a topically acceptable carrier. Examples of suitable carriers include an oil, cream, dispersion, emulsion, gel, ointment, lotion, milk, mouse, spray or tonic. The dermatologically acceptable carrier can contain water. For example, the dermatologically acceptable carrier can be a natural oil, such as terpene, such as squalene. In one embodiment, the dermatologically acceptable carrier is squalene. Water and squalene are also present in the human skin and both play a part in the skins natural UV protection system. Squalene reacts with reactive oxygen species to reduce and form squalene monohydroperoxide isomers.

One advantage of the compositions of the disclosure, per an embodiment, is that they provide for the absorption of byproducts of reactive oxygen species (ROS), commonly associated with ultraviolet irradiation of titanium oxides. Like titanium oxide nanoparticles used in sunscreens, Ti MOFs have photochromic cyclic octamers of TiO2 octahedra, resulting in the UV irradiation reduction of Ti(IV) to Ti(III) and generation of reactive oxygen species.

In one embodiment, the titanium metal organic framework is able to absorb the byproducts of ROS after ultraviolet irradiation. For example, the composition comprising MIL-125NH$_2$, which is known to be stable after UV exposure, can adsorb carbon radical species generated when the organic topical carrier or natural skin secretion, in this case squalene, reduces to squalene monohydroperoxide isomers in the presence of ROS. For example, the composition comprising MIL-125NH$_2$ and Squalene showed reduced isomers of Squalene after UV exposure and no isomers of squalene monohydroperoxide isomers through gas chromatography-mass spectrometry (GC-MS) analysis. For example, the composition comprising MIL-125NH$_2$ can adsorb hydroxyl radicals generated when the organic topical carrier or natural skin secretion, in this case water, reduces to hydrogen peroxides in the presence of ROS. For example, the MIL-125NH$_2$ is shown to absorb 218.2% of its weight of a solution of thirty percent tert-butyl hydroperoxide and water. An embodiment therefore provides a UV absorptive composition, e.g. a sunscreen composition, which can additionally absorb byproducts commonly associated with ultraviolet irradiation.

According to another embodiment, a method is provided of protecting skin from the effect of IN radiation comprising administering an effective amount of a composition comprising a titanium MOF and a dermatologically acceptable carrier.

In one embodiment, the composition is administered topically.

In one embodiment, the method involves a composition as defined herein, in particular as defined in the claims.

In one embodiment, the method also absorbs byproducts of reactive oxygen species such as organic peroxides, hydroxyl radicals, or carbon radicals. This is achieved through the inclusion of the titanium MOF, In one embodiment, the method comprises converting hydroxyl radicals into a superoxide radical and/or hydrogen peroxides.

In one embodiment, the method comprises converting carbon radicals into peroxy acids, peroxy esters, and/or diacyl peroxides. In one embodiment, the method comprises converting carbon radicals into a tocopheroxy radical, tocopheryl radical and/or squalene monohydroperoxide isomers.

Examples

Synthesis of MIL-125NH$_2$

MIL-125NH$_2$ MOF was prepared using 300 g of 2-aminoterephthalic acid (ligand), 150 mL Titanium (IV) isopropoxide 98+%, 8.1 L DMF, 900 mL Methanol. A 10 L reactor was heated to 120° C. 300 g of ligand was dissolved in 4.5 L of DMF while stirring and heating in a glass container until a uniform solution was obtained. This solution was added to the heated reactor. Then, in a 500 mL glass flask, 150 mL of Titanium (IV) isopropoxide was dissolved in another 3.5 mL of DMF. To the reactor, 900 mL of methanol was added, along with 100 mL of DMF. This caused the ligand to completely dissolve. The dissolved titanium isopropoxide/DMf solution was added to the mixture in the reactor and the temperature of the oil surrounding the reactor, was increased to 150° C. The mixture was stirred and heated in the reaction at 150° C. for 48 hours where after it was cooled to room temperature. The yellow solid was then filtered using a Nutsche, washed in methanol and filtered once more, leaving a dry yellow powder. The resulting surface area is SBET=1289 m2/g.

Synthesis of MIL-177HT

MIL-177-HT was prepared using a 25 mL round bottom flask where 200 mg of H4mdip with 10 mL of formic acid was added and stirred at room temperature until it was a uniform solution. Following that, 400 µL of Ti(iPrO)4 was added drop wise using a micropipette. The reaction was heated under reflux for 24 hours and then cooled to room temperature. Then, the white solid was filtered using vacuum filtration and washed with ethanol, where after it was filtered once more. In order to create the 'HT' part of the MOF, 200 mg of the MOF was grounded into a fine powder, transferred to a flat glass dish, and dispersed uniformly. It was then heated in an oven at 280° C. for 12 hours, forming a dark yellow/nude colored powder. The resulting surface area is SBET=690 m2/g.

Squalene

Olive Squalene was purchased from Natural Sourcing, LLC, with an advertised concentration of 88.12%, a density of 0.86 g/L, and an acidity of 0.02 mg KOH/kg in the form of a pale yellow liquid oil.

Oxybenzone

2-Hydroxy-4-methoxybenzophenone 98% (Oxybenzone) was purchased from Sigma Aldrich. It was dissolved in Hexane (HPLC grade, 98.5% pure hexane isomers) at a solubility level of 50 mg/mL.

Composition 1

In a 25 mL glass vial, 20 mL of Squalene was measured out using a micropipette. To the same vial, 0.001 g of MIL-125-NH$_2$ was added. The mixture was stirred vigorously until a light yellow, and uniform solution was obtained. The weight percent of the MIL-125-NH$_2$ was 0.0058% of the composition.

Composition 2

In a 25 mL glass vial, 20 mL of Squalene was measured out using a micropipette. To the same vial, 0.0505 g of MIL-125NH$_2$ was added. The mixture was stirred vigorously until a yellow, and uniform solution was obtained. The weight percent of the MIL-125NH$_2$ was 0.293% of the composition.

Composition 3

In a 25 mL glass vial, 20 mL of Squalene was measured out using a micropipette. To the same vial, 0.100 g of MIL-125NH$_2$ was added. The mixture was stirred vigorously until a dark yellow, and uniform solution was obtained. The weight percent of the MIL-125NH$_2$ was 0.579% of the composition.

Composition 4

In a 25 mL glass vial, 20 mL of Squalene was measured out using a micropipette. To the same vial, 0.0505 g of MIL-177HT was added. The mixture was stirred vigorously until a light brown, and uniform solution was obtained. The weight percent of the MIL-177HT was 0.293% of the composition.

Composition 5

The Oxybenzone solution was prepared by measuring out 1.25 g of 2-Hydroxy-4-methoxybenzophenone. In a 30 mL flask, 25 mL of Hexane (HPLC grade) was added. The 2-Hydroxy-4-methoxybenzophenone was added to the 30 mL flask. In a 25 mL glass vial, 20 mL of Oxybenzone solution was measured out using a micropipette. To the same vial, 0.0505 g of MIL-125-NH$_2$ was added. The mixture was stirred vigorously until a light yellow, and uniform solution was obtained. The weight percent of the MIL-125NH$_2$ was 0.20998% of the composition.

GC-MS Analysis of Squalene Oxidation

Squalene and Composition 3 were tested under a GC-MS for isomers of Squalene, and isomers of squalene monohydroperoxide (SQOOH), which include 2-OOH-SQ, 3-OOH-SQ, 6-OOH-SQ, 10-OOH-SQ, 7-OOH-SQ, and 11-OOH-SQ.

UV Testing

Compositions 1, 2, 3, 4, and 5 were tested using SHIMADZU UV-Vis spectrometers UV-2450, UV-2550 to observe the absorption (0 to 3) over a wavelength of 200 nm to 700 nm. In five different quartz cuvettes labeled 1-5, 5 µL of sample 1, 2, 3, 4, and 5 was added, respectively. All of the samples were inserted into the single cell slot and tested using the specified spectrometer.

Hydrogen Peroxide Absorption Testing

In a 25 mL glass vial, 20 mL of tert-butyl hydroperoxide (70% in water) was measured out using a micropipette. To the same vial, 0.100 g of MIL-125-NH$_2$ was added. The solution was allowed to air dry for eight hours. The weight of the dry material MIL-125-NH$_2$ increased to 0.3182 g.

All the features and advantages, including structural details, spatial arrangements and method steps, which follow from the claims, the description and the drawing can be fundamental to the invention both on their own and in different combinations. It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

What is claimed:

1. A sunscreen composition of a cosmetic composition for topical application comprising a titanium metal organic framework and squalene, wherein the titanium metal organic framework is between 0.001 wt % and less than 25 wt % of the composition.

2. The composition of claim 1, where the titanium metal organic framework is a carboxylate-based metal organic framework.

3. The composition of claim 2, wherein the carboxylate ligand is selected from:

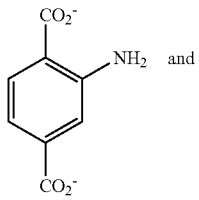

and

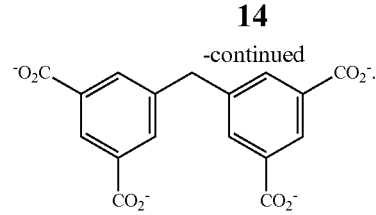

4. The composition of claim 1, wherein the titanium metal organic framework absorbs ultra violet light.

5. The composition of claim 1, wherein the titanium metal organic framework adsorbs byproducts of Reactive Oxygen Species.

6. The composition of claim 5, wherein the byproducts of Reactive Oxygen Species are hydroxyl radicals or carbon radicals.

7. The composition of claim 6, wherein the byproducts of Reactive Oxygen Species are hydroxyl radicals resulting in a superoxide radical and/or hydrogen peroxides.

8. The composition of claim 6, wherein the byproducts of Reactive Oxygen Species are carbon radicals resulting in peroxy acids. peroxy esters, diacyl peroxides.

9. The composition of claim 6, wherein the byproducts of Reactive Oxygen Species are carbon radicals resulting in Tocopheroxyl radical, Tocopheryl radical and/or Squalene monohydroperoxide isomers.

10. The composition of claim 5, wherein the byproducts of Reactive Oxygen Species are organic peroxides.

11. The composition of claim 1, wherein the titanium metal organic framework comprises at least one metal ion coordinated to at least one aromatic di-, tri-, or tetracarboxylic acid.

12. The composition of claim 1, wherein the titanium metal organic framework has a surface area greater than 200 m$^2$/g BET.

13. The composition of claim 1, wherein the titanium metal organic framework has an average pore size between 5 Å and 50 Å.

14. The composition of claim 1, wherein the titanium metal organic framework is a photo catalyst.

15. The composition of claim 1, wherein the titanium metal organic framework scatters UV light.

16. The composition of claim 1, wherein water is present.

17. A method of protecting skin from the effect of UV radiation comprising administering an effective amount of the composition according to claim 1.

18. The method of claim 17, wherein the composition is administered topically.

19. The composition of claim 1, wherein the titanium metal organic framework is between 0.005 wt % and 0.600 wt %.

* * * * *